US011617731B2

(12) United States Patent
Carroll et al.

(10) Patent No.: US 11,617,731 B2
(45) Date of Patent: *Apr. 4, 2023

(54) AMINO ACID COMPOSITIONS AND THEIR USE FOR THE TREATMENT OF TRAUMATIC BRAIN INJURY

(71) Applicant: AXCELLA HEALTH INC., Cambridge, MA (US)

(72) Inventors: Sean Carroll, Cambridge, MA (US); Raffi Afeyan, Boston, MA (US); Gianluca De Rienzo, Brookline, MA (US); Matthew Russell, West Newton, MA (US)

(73) Assignee: AXCELLA HEALTH, INC., Cambridge, MA (US)

( * ) Notice: Subject to any disclaimer, the term of this patent is extended or adjusted under 35 U.S.C. 154(b) by 80 days.

This patent is subject to a terminal disclaimer.

(21) Appl. No.: 16/608,349

(22) PCT Filed: Apr. 27, 2018

(86) PCT No.: PCT/US2018/029908
§ 371 (c)(1),
(2) Date: Oct. 25, 2019

(87) PCT Pub. No.: WO2018/201024
PCT Pub. Date: Nov. 1, 2018

(65) Prior Publication Data
US 2020/0163919 A1 May 28, 2020

Related U.S. Application Data

(60) Provisional application No. 62/491,796, filed on Apr. 28, 2017.

(51) Int. Cl.
*A61K 31/198* (2006.01)
*A61K 31/401* (2006.01)

(52) U.S. Cl.
CPC .......... *A61K 31/198* (2013.01); *A61K 31/401* (2013.01)

(58) Field of Classification Search
CPC ............................ A61K 31/198; A61K 31/401
See application file for complete search history.

(56) References Cited

U.S. PATENT DOCUMENTS

| | | |
|---|---|---|
| 4,438,144 A | 3/1984 | Blackburn |
| 6,864,242 B2 * | 3/2005 | Ernest ...................... A61P 3/02 514/561 |
| 9,101,580 B2 | 8/2015 | Bennett et al. |
| 9,289,404 B2 | 3/2016 | Kopke et al. |
| 9,642,823 B2 | 5/2017 | Kopke et al. |
| 9,878,004 B2 | 1/2018 | Williams et al. |
| 10,201,513 B2 | 2/2019 | Hamill et al. |
| 10,238,617 B2 | 3/2019 | Hamill et al. |
| 10,471,034 B2 | 11/2019 | Hamill et al. |
| 10,596,136 B2 | 3/2020 | Chakravarthy et al. |
| 2005/0107338 A1 | 5/2005 | Seidman |
| 2006/0128778 A1 * | 6/2006 | Abe ...................... A61K 31/198 514/400 |
| 2007/0286909 A1 * | 12/2007 | Smith .................. A61K 31/455 424/682 |
| 2013/0090356 A1 | 4/2013 | Kaiser |
| 2014/0255511 A1 | 9/2014 | Dardevet et al. |
| 2016/0339078 A1 | 11/2016 | Hamill et al. |
| 2017/0202797 A1 | 7/2017 | Kopke et al. |
| 2017/0281583 A1 | 10/2017 | Kopke et al. |
| 2018/0125926 A1 | 5/2018 | Williams et al. |
| 2018/0133185 A1 | 5/2018 | Cohen |
| 2018/0169044 A1 | 6/2018 | Hamill et al. |
| 2018/0169045 A1 | 6/2018 | Hamill et al. |
| 2018/0169046 A1 | 6/2018 | Hamill et al. |
| 2018/0169047 A1 | 6/2018 | Hamill et al. |
| 2018/0207118 A1 | 7/2018 | Hamill et al. |
| 2018/0207119 A1 | 7/2018 | Hamill et al. |
| 2018/0296516 A1 | 10/2018 | Hamill et al. |
| 2019/0046486 A1 | 2/2019 | De Rienzo et al. |
| 2019/0046487 A1 | 2/2019 | Comb et al. |
| 2019/0105294 A1 | 4/2019 | Hamill et al. |
| 2019/0247351 A1 | 8/2019 | Comb et al. |
| 2019/0388374 A1 | 12/2019 | Hanlon et al. |
| 2019/0388375 A1 | 12/2019 | Hanlon et al. |
| 2019/0388376 A1 | 12/2019 | Carroll et al. |
| 2019/0388377 A1 | 12/2019 | Hamill et al. |
| 2020/0016104 A1 | 1/2020 | Chakravarthy et al. |

FOREIGN PATENT DOCUMENTS

| | | |
|---|---|---|
| EP | 1552826 A1 | 7/2005 |
| EP | 2091526 B1 | 5/2011 |
| WO | 2006102451 A2 | 9/2006 |
| WO | 2012106654 A1 | 8/2012 |
| WO | 2014172341 A1 | 10/2014 |

(Continued)

OTHER PUBLICATIONS

Raphael N. Vuille-Dit-Bille et al., 43(3) Amino Acids 1287-1296 (2012) (Year: 2012).*
"Mechanisms of Neuroinflammation" (Abreu, ed.) InTechOpen (2017) Chapter 9: Roles of Pro- and Anti-inflammatory Cytokines in Traumatic Brain Injury and Acute Ischemic Stroke (Dugue et al.) pp. 211-261.
"Sports-Related Concussions in Youth: Improving the Science, Changing the Culture," (Robert Graham et al. eds., 2014) The National Academies Press, Washington, DC.
Traumatic and Ischemic Injury: Methods and Protocols, Methods in Molecular Biology, vol. 1717 (Binu Thatakan, ed.) Springer (2018) Chapter 17: An In Vitro Model of Traumatic Brain Injury (Salvador et al.) pp. 219-227.
Abbasi et al., "Acetyl-L-Carnitine as an Adjunctive Therapy in the Treatment of Attention-Deficit/Hyperactivity Disorder in Children and Adolescents: A Placebo-Controlled Trial," Child Psychiatry Hum Dev (2011) vol. 42, pp. 367-375.

(Continued)

*Primary Examiner* — Timothy R Rozof
(74) *Attorney, Agent, or Firm* — K&L Gates LLP

(57) ABSTRACT

This disclosure provides pharmaceutical compositions comprising defined amino acid components, and methods for treating traumatic brain injury comprising administering an effective amount of the compositions to a subject in need thereof.

8 Claims, No Drawings

(56) References Cited

FOREIGN PATENT DOCUMENTS

| | | |
|---|---|---|
| WO | 2015048333 A2 | 4/2015 |
| WO | 2015048340 A2 | 4/2015 |
| WO | 2015048342 A2 | 4/2015 |
| WO | 2015048345 A2 | 4/2015 |
| WO | 2015048346 A2 | 4/2015 |
| WO | 2015048348 A2 | 4/2015 |
| WO | 2018118941 A1 | 6/2018 |
| WO | 2018118957 A1 | 6/2018 |
| WO | 2018201024 A1 | 11/2018 |

OTHER PUBLICATIONS

Adeleye et al., "D-Cycloserine Improves Functional Outcome after Traumatic Brain Injury with Wide Therapeutic Window," Eur J Pharmacol (2010) vol. 629, Nos. 1-3, pp. 25-30.

Alawieh et al., "Targeted complement inhibition salvages stressed neurons and inhibits neuroinflammation after stroke in mice," Sci Transl Med (2018) vol. 10, Article eaao6459, 13 pages.

Aldini et al., "N-Aceytlcysteine as an antioxidant and disulphide breaking agent: the reasons why," Free Radical Research (2018) vol. 52, No. 7, pp. 751-762.

Alexandrov et al., "High-throughput analysis of behavior for drug discovery," Europea Journal of Pharmacology (2015) Vo. 750, pp. 82-89.

Allen et al., "Creatine metabolism and psychiatric disorders: Does creatine supplementation have therapeutic value?" Neurosci Biobehav Rev (2012) vol. 36, No. 5, pp. 1442-1462.

Amen et al., "Reversing brain damage in former NFL players: implications for traumatic brain injury and substance abuse rehabilitation," J Psychoactive Drugs (2011) vol. 43, No. 1, 5 pages. Abstract Only.

Aquilani et al., "Branched-Chain Amino Acids Enhance the Cognitive Recovery of Patients With Severe Traumatic Brain Injury," Arch Phys Med Rehabil (2005) vol. 86, pp. 1729-1735.

Aquilani et al., "Effect of calorie-protein supplementation on the cognitive recovery of patients with subacute stroke," Nutritional Neuroscience (2008) vol. 11, No. 5, pp. 235-240.

Aquilani et al., "Peripheral Plasma Amino Acid Abnormalities in Rehabilitation Patients With Severe Brain Injury," Arch Phys Med Rehabil (2000) vol. 81, pp. 176-181.

Aquilani et al., "Protein supplementation may enhance the spontaneous recovery of neurological alterations in patients with ischaemic stroke," Clinical Rehabilitation (2008) vol. 22, pp. 1042-1050.

Ates et al., "Antioxidant and free radical scavenging properties of N-acetylcysteine amide (NACA) and comparison with N-acetylcysteine (NAC)," Free Radical Research (2008) vol. 42, No. 4, pp. 372-377.

Ayuso et al., "Advanced neuroprotection for brain ischemia: an alternative approach to minimize stroke damage," Expert Opin Investig Drugs (2015) vol. 24, No. 9, pp. 1137-1142.

Baskaya et al., "Neuroprotective effects of citicoline on brain edema and blood-brain barrier breakdown after traumatic brain injury," J Neurosurg (2000) vol. 92, pp. 448-452.

Becker et al., "Does traumatic brain injury hold the key to the Alzheimer's puzzle?" Alzheimer's & Dementia (2017) doi: 10.1016/j.jalz.2017.11.007, 13 pages.

Benarroch et al., "Blood-brain barrier: Recent developmnts and clinical correlations," Neurology (2012) vol. 78, pp. 1268-1276.

Berkhemer et al., "A Randomized Trial of Intaarterial Treatment for Acute Ischemic Stroke," N Engl J Med (2015) vol. 372, No. 1, pp. 11-20.

Blennow et al., "Traumatic brain injuries," Nat Rev Dis Primers (2016) vol. 2, Article 16084, 19 pages.

Bondi et al., "Found in translation: Understanding the biology and behavior of experimental traumatic brain injury," Neurosci Biobehav Rev (2014) doi: 10 1016/j.neubiorev.2014212.004, 24 pages.

Brooks et al., "The Use of an Electrophysiological Brain Function Index in the Evaluation of Concussed Athletes," J head Trauma Rehabil (2018) vol. 33, No. 1, pp. 1-6.

Brustovetsky et al., "Calcium-induced Cytochrome c release from CNS mitochondria is associated with the premeability transition and rupture of the outer membrane," Journal of Neurochemistry (2002) vol. 80, pp. 207-218.

Børsheim et al., "Plasma Amino Acid Concentrations During Late Rehabilitation in Patients With Traumatic Brain Injury," Arch Phys Med Rehabil (2007) vol. 88, pp. 234-238.

Carron et al., "Traumatic Brain Injury and Neuronal Functionality Changes in Sensory Cortex," Frontiers in Systems Neuroscience (2016) vol. 10, Article 47, 17 pages.

Cassella et al., "Ischemic Stroke: Advances in Diagnosis and Management," Emerg Med Clin N Am (2017) vol. 35, pp. 911-930.

Chamorro et al., "The immunology of acute stroke," Nat Rev Neurol (2012) vol. 8, pp. 401-410.

Chen et al., "In-Vitro Approaches for Studying Blast-Induced Traumatic Brain Injury," Journal of Neurotrauma (2009) vol. 26, pp. 861-876.

Chen et al., "The fate of medications evaluated for ischemic stroke pharmacotherapy over the period 1995-2015," Acta Pharmaceutica Sinica B (2016) vol. 6, No. 6, pp. 522-530.

Cherian et al., "Neuroprotective Effects of L-Arginine Administration after Cortical Impact Injury in Rats: Dose Response and Time Window," J Pharmacol Exp Ther (2003) vol. 304, No. 2, pp. 617-623.

Cherry et al., "CCL11 is increased in the CNS in chronic traumatic encephalopathy but not in Alzheimer's disease," PLOS One (2017) vol. 12, No. 9, Article e0185541, 14 pages.

Chiu et al., "Peptide Pharmacological Approaches to Treating Traumatic Brain Injury: a Case for Arginine-Rich Peptides," Mol Neurobiol (2017) vol. 54, pp. 7838-7857.

Clark et al., "Phase I randomized clinical trial of N-acetylcysteine in combination with an adjuvant probenecid for treatment of severe traumatic brain injury," PLOS One (2017) vol. 12, No. 7, Article e0180280, 16 pages.

ClincalTrials.gov Identifier: NCT00822263 "The Use of Antioxidants to Reduce Sequela of Mild Traumatic Brain Injury (mTBI) After Blast Exposure," Clinicaltrials.gov, last updated Aug. 10, 2010.

ClincalTrials.gov Identifier: NCT01320527 "A Clinical Trial of a Vitamin/Nutriceutical Formulation for Alzheimer's Disease" Clinicaltrials.gov, last updated Mar. 3, 2016.

ClincalTrials.gov Identifier: NCT01515839 "Single Photon Emission Computed Tomography (SPECT) Imaging Study of Professional American Football Players" Clinicaltrials gov, last updated Jan. 24, 2012.

ClincalTrials.gov Identifier: NCT01860404 "BCAA's in Concussion (Hit Heads)," Clinicaltrials.gov, first posted May 22, 2013, last updated Jul. 20, 2018.

ClinicalTrials.gov Identifier: NCT03241732 "PET-MRI and the Effect on N-Acetyl Cysteine (NAC) and Anti-Inflammatory Diet in Traumatic Brain Injury," first posted Aug. 7, 2017, last updated Jan. 17, 2018.

Cole et al., "Craniotomy: True Sham for Traumatic Brain Injury, or a Sham of a Sham?" Journal of Neurotrauma (2011) vol. 28, pp. 659-369.

Cole et al., "Dietary branched chain amino acids ameliorate injury-induced cognitive impairment," PNAS (2010) vol. 107, No. 1, pp. 366-371.

Covassin et al., "Sex Differences in Reported Concussion Injury Rates and Time Loss From Participation: An Update of the National Collegiate Athletic Association Injury Surveillance Program From 2004-2005 Through 2008-2009," Journal of Athletic Training (2016) vol. 51, No. 3, pp. 189-194.

Dash et al., "Traumatic Brain Injury Alters Methionine Metabolism: Implications for Pathophysiology," Front Syst Neurosci (2016) vol. 10, Article 36, 10 pages.

Dean et al., "N-acetylcysteine in psychiatry: current therapeutic evidence and potential mechanisms of action," J Psychiatry Neurosci (2011) vol. 32, No. 2, pp. 78-86.

Dean et al., "Potential for use of creatine supplementatoin following mild traumatic brain injury," Concussion (2017) doi: 10.2217/cnc-2016-0016, 15 pages.

(56) References Cited

OTHER PUBLICATIONS

Deepmala et al., "Clinical trials of N-acetylcysteine in psychiatry and neurology: A systematic revew," Neurosci Biobehav Rev (2015) vol. 55, pp. 294-321.
Dickens et al., "Serum metabolites associate with CT findings following TBI," Journal of Neurotrauma (2017) doi: 10.1089/neu.2017.5272, 40 pages.
Dickstein et al., "Cerebral [18F]T087/AV1451 retention pattern in clinically probable CTE resembles pathognomonic distribution of CIE tauopathy," Transl Psychiatry (2016) vol. 6, Article e900, 8 pages.
Duan et al., "Ca2+-dependent generation of mitochondrial reactive oxygen species serves as a signal for poly(ADP-ribose) polymerase-1 activation during glutamate excitotoxicity," J Physiol (2007) vol. 585, No. 3, pp. 741-758.
Duclos et al., "Rest-Activity Cycle Disturbances in the Acute Phase of Moderate to Severe Traumatic Brain Injury," Neurorehabilitation and Neural Repair (2014) vol. 28, No. 5, pp. 472-482.
Eakin et al., "Efficacy of N-Acetyl Cysteine in Traumatic Brain Injury," PLOS One (2014) vol. 9, Issue 4, Article e90617, 7 pages.
Elkind et al., "Efficacy, dosage, and duration of action of branched chain amino acid therapy for traumatic brain injury," Frontiers in Neurology (2015) vol. 6, Article 73, 6 pages.
Ferreira et al., "L-Camitine and Acetyl-L-carnitine Roles and Neuroprotection in Developing Brain," Neurochem Res (2017) doi: 10.1007/s11064-017-2288-7, 15 pages.
Ferrero et al., "CNS findings in chronic fatigue syndrome and a neuropathological case report," J Investig Med (2017) doi: 10.1136/jim-2016-000390, 10 pages.
Fu et al., "Hyperbaric oxygen treatment and enteral nutrition support with glutamine relieves traumatic brain injury in the rats," Int J Clin Exp Med (2014) vol. 7, No. 12, pp. 5686-5690.
Ganguly et al., "Evaluation of the Stability of Creatine in Solution Prepared From Effervescent Creatine Formulations," AAPS PharmSciTech (2003) vol. 4, No. 2, Article 25, 10 pages.
Gibson et al., "Feasability of progesterone treatment for ischemic stroke," Journal of Cerebral Blood Flow & Metabolism (2016) vol. 26, No. 3, pp. 487-491.
Gibson et al., "Traumatic brain injury and the effects of diazepam, diltiazem, and MK-801 on GABA-A receptor subunit expression in rat hippocampus," Journal of Biomedical Science (2010) vol. 17, Article 38, 11 pages.
Gil et al., "Aripiprazole exerts a neuroprotective effect in mouse focal cerebral ischemia," Experimental and Therapeutic Medicine (2018) vol. 15, pp. 745-750.
Gill et al., "Acute plasma tau relates to prolonged return to play after concussion," Neurology (2017) vol. 88, p. 1-8.
Gill et al., "Higher exosomal tau, amyloid-beta 42 and IL-10 are associated with mild TBIs and chronic symptoms in military personnel," Brain Injury (2018) doi: 10.1080/02699052.2018.1471738, 8 pages.
Ginsburg, "Neuroprotection for Ischemic Stroke: Past, Present, and Future," Neuropharmacology (2008) vol. 55, No. 3, pp. 363-389.
Gualano et al., "Effects of creatine supplementation of glucose tolerance and insulin sensitivity in sedentary healthy males undergoing aerobic training," Amino Acids (2008) vol. 34, pp. 245-250.
Gualano et al., "In sickness and in health: the widespread application of creatine supplementation," Amino Acids (2012) vol. 43, pp. 519-529.
Guerriero et al., "Glutamate and GABA Imbalance Following Traumatic Brain Injury," Curr Neurol Neurosci Rep (2015) vol. 15, No. 27, doi: 10.1007/s11910-015-0545-1, 11 pages.
Gurkoff et al., "Voltage-Gated Calcium Channel Antagonists and Traumatic Brain Injury," Pharmaceuticals (2013) vol. 6, pp. 788-812.
Haber et al., "Minocycline plus N-acetylcysteine induces remyelination, synergistically protects oligodendrocytes, and modifies meuroinflammation in a rat model of mild traumatic brain injury," Journal of Cerebral Blood Flow & Metabolism (2017) doi: 10.1177/00271678X17718106, 15 pages.
Haber et al., "Minocycline plus N-acytlcysteine synergize to modulate inflammation and prevent cognitive and memory deficits in a rat model of mild traumatic brain injury," Experimental Neurology (2013) vol. 249, pp. 169-177.
Hammett et al., "Dietary supplementation of creatine monohydrate reduces the human fMRI BOLD signal," Neuroscience Letters (2010) vol. 479, pp. 201-205.
Hoane et al., "Administration of Riboflavin Improves Behavioral Outcome and Reduces Edema Formation and Glial Fibrillary Acidic Protein Expression after Traumatic Brain Injury," Journal of Neurotrauma (2005) vol. 22, No. 10, pp. 1112-1122.
Hoffer et al., "Amelioration of Acute Sequelae of Blast Induced Mild Traumatic Brain Injury by N-Acetyl Cysteine: A Double-Blind, Placebo Controlled Study," PLOS One (2013) vol. 8, Issue 1, Article e54163, 10 pages.
Hoffer et al., "Repositioning drugs for traumatic brain injury-N-acetyl cysteine and Phenserine," J Biomed Sci (2017) vol. 24, No. 71, 15 pages.
International Search Report and Written Opinion issued in PCT/US2018/029908, dated Jul. 17, 2018.
International Search Report and Written Opinion issued in PCT/US2018/046559, dated Nov. 21, 2018.
Jalal et al., "Acetyl-L-carnitine reduces the infarct size and striatal glutamate outflow following focal cerebral ischemia in rats," Ann NY Acad Sci (2010) vol. 1199, pp. 95-104.
Jeter et al., "Human Mild Traumatic Brain Injury Decreases Circulating Branched-Chain Amino Acids and Their Metabolite Levels," Journal of Neurotrauma (2013) vol. 30, pp. 671-679.
Johnston et al., "Medical and Neurological Complications of Ischemic Stroke: Experience From the RANTTAS Trial," Stroke (1998) vol. 29, pp. 447-453.
Jouvei et al., "Branched Chain Amino Acids Induce Apoptosis in Neural Cells without Mitochondrial Membrane Depolarization or Cytochrome c Release: Implications for Neurological Impairment Associated with Maple Syrup Urine Disease," Molecular Biology of the Cell (2000) vol. 11, pp. 1919-1932.
Kadhim et al., "Cytokines and Brain Injury: Invited Review," Journal of Intensive Care Medicine (2008) vol. 23, No. 4, pp. 236-249.
Karalija et al., "Neuroprotective Effects of N-Acetyl-Cysteine and Acetyl-L-Carnitine after Spinal Cord Injury in Adult Rats," PLoS One (2012) vol. 7, Issue 7, Article e41086, 11 pages.
Karalija et al., "The Effects of N-Acetyl-Cysteine and Acetyl-L-Carnitine on Neural Survival, Neuroinflammation and Regeneration Following Spinal Cord Surgery," Neuroscience (2014) vol. 269, pp. 143-151.
Kawata et al., "Acute changes in plasma total Tau levels are independent of subconcussive head impacts in college football players," Journal of Neurotrauma (2017) doi: 10.1089/neu.2017.5376, 25 pages.
Kawata et al., "Subconcussive impact-dependent increase in plasma S100 levels in collegiate football players," Journal of Neurotrauma (2016) doi: 10.1089/neu.2016.4786, 35 pages.
Kimberly et al., "Metabolite Profiling Identifies a Branched Chain Amino Acid Signature in Acute Cardioembolic Stroke," Stroke (2013) vol. 44, doi: 10.1161/STROKEAHA.111.000397, 20 pages.
Kondoh et al., "Lysine and arginine reduce the effects of cerebral ischemic insults and inhibit glutamate-induced neuronal activity in rats," Frontiers in Integrative Neuroscience (2010) vol. 4, Article 18, 10 pages.
Kreitzer et al., "Systematic Review of caregiver and dyad interventions following adult traumatic brain injury," Archives of Physical Medicine and Rehabilitation (2018) doi: 10.1016/j.apmr.2018.04.016, 42 pages.
Krzyzanowska et al., "N-Acetylcysteine and Ceftriaxone as Preconditioning Strategies in Focal Brain Ischemia: Influence on Glutamate Transporters Expression," Neurotox Res (2016) vol. 29, pp. 539-550.
Lau et al., "Inhibition of Caspase-Mediated Apoptosisby Peroxynitrite in Traumatic Brain Injury," The Journal of Neuroscience (2006) vol. 26, No. 45, pp. 11540-11553.

(56) References Cited

OTHER PUBLICATIONS

Ley et al., "In Vivo Effect of Propranolol Dose and Timing on Cerebral Perfusion After Traumatic Brain Injury," J Trauma (2010) vol. 68, pp. 353-356.
Lim et al., "Dietary Therapy Mitigates Persistent Wake Deficits Caused by Mild Traumatic Brain Injury," Sci Transl Med (2013) vol. 5, No. 215, doi: 10.1126/scitranslmed.3007092, 22 pages.
Lolic et al., "Neuroprotective Effects of Acetyl-L-Carnitine After Stroke in Rats," Annals of Emergency Medicine (1997) vol. 29, pp. 758-765.
Lopez et al., "Resveratrol Neuroprotection in Stroke and Traumatic CNS injury," Neurochem Int (2015) vol. 89, pp. 75-82.
Louin et al., "Plasma concentrations of arginine and related amino acids following traumatic brain injury: Proline as a promising biomarker of brain damage severity," Nitric Oxide (2007) vol. 17, pp. 91-97.
Luo et al., "CART peptide induces neuroregeneration in stroke rats," Journal of Cerebral Blood Flow & Metabolism (2013) vol. 33, pp. 300-310.
Mahmoodpoor et al., "A pilot trial of L-carnitine in patients with traumtic brain injury: Effects on biomarkers of injury," Journal of Critical Care (2018) vol. 45, pp. 128-132.
Majid, "Neuroprotection in Stroke: Past, Present, and Future," ISRN Neurology (2014) vol. 2014, Article 515716, 17 pages.
Malaguarnera et al., "Branched chain amino acids supplemented with L-acetylcarnitine versus BCAA treatmentin hepatic coma: a randomized and controlled double blind study," Eur J Gastroenterol Hepatol (2009) vol. 21, No. 7, pp. 762-770, Abstract Only.
Mardinoglu et al., "Personal model-assisted identification of NAD+ and glutathione metabolism as interventiontarget in NAFLD," Molecular Systems Biology (2017) vol. 13, Article 916, 17 pages.
Martina et al., "Long-Term N-Acetylcysteine and L-Arginine Administration Reduces Endothelial Activation and Systolic Blood Pressure in Hyptertensive Patients With Type 2 Diabetes," Diabetes Care (2008) vol. 31, No. 5, pp. 940-944.
Martinez de Lizarrondo et al., "Potent Thrombolytic Effect of N-Aceytlcysteine on Arterial Thrombi," Circulation (2017) VI. 136, pp. 646-660.
Mei et al., "Huperzine A alleviates neuroinflammation, oxidative stress and improves cognitive function after repetitive traumatic brain injury," Metab Brain Dis (2017) doi: 10.1007/s11011-017-0075-4, 9 pages.
Minnerup et al., "Neuroprotection for Stroke: Current Status and Future Perspectives," Int J Mol Sci (2012) vol. 13, pp. 11753-11772.
Moghaddas et al., "L-Carnitine and Potential Protective Effects Against Ischemia-Reperfusion Injury in Noncardiac Organs: From Experimental Data to Potential Clinical Approaches," Journal of Dietary Supplements (2017) doi: 10.1080/19390211.2017.1359221, 17 pages.
Mokhtari et al., "Effect of Memantine on Serum Levels of Neuron-Specific Enolase and on the Glasgow Coma Scale in Patients With Moderate Traumatic Brain Injury," The Journal of Clinical Pharmacology (2018) vol. 58, No. 1, pp. 42-47.
Molnar et al., "The L-arginine Pathway in Acute Ischemic Stroke and Severe Cartoid Stenosis: Temporal Profiles and Association with Biomarkers and Outcome," Journal of Stroke and Cerebrovascular Diseases (2014) vol. 23, No. 8, pp. 2206-2214.
Mondello et al., "Serum Concentrations of Ubiquitin C-Terminal Hydrolase-L1 and Glial Fibrillary Acidic Protein after Pediatric Traumtic Brain Injury," Nat Sci Rep (2016) vol. 6, Article 28203, 8 pages.
Monti et al., "N-Acetyl Cysteine May Support Dopamine Neurons in Parkinson's Disease: Preliminary Clinical and Cell Line Data," PLOS One (2016) vol. 11, No. 6, Article e0157602, 15 pages.
Moretti et al., "Neuroprotection for ischaemic stroke: Current status and challenges," Pharmacology and Therapeutics (2014) doi: 10 1016/j.pharmthera.2014.09.003, 54 pages.
Morrison et al., "An in vitro model of traumatic brain injury utilising two-dimensional stretch of organotypic hippocampal slice cultures," Journal of Neuroscience Methods (2006) vol. 150, pp. 192-201.
Nelson et al., "Acute Clinical Predictors of Symptom Recovery in Emergency Department Patients with Uncomplicated Mild Traumatic Brain Injury (mTBI) or Non-TBI Injuries," Journal of Neurotrauma (2017) doi: 10.1089/neu.2017.4988, 42 pages.
Neuhaus et al., "Importance of Preclinical Research in the Development of Neuroprotective Strategies for Ischemic Stroke," JAMA Neurology (2014) vol. 71, No. 5, pp. 634-639.
Neuhaus et al., "Neuroprotection in stroke: the importance of collaboration and reproducibility," Brain (2017) doi: 10.1093/brain/awx126, 14 pages.
Nutrition and Traumatic Brain Injury: Improving Acute and Subacute Health Outcomes in Military Personnel (Erdman et al., eds.) Institute of Medicine of the National Academies, National Academies Press, Washington D.C. 2011. pp. 1-10, 55-68, 88-107, 108-114, 130-139 and 249-256.
Oliver et al., "Protection Before Impact: the Potential Neuroprotective Role of Nutritional Supplementation in Sports-Related Head Trauma," Sports Med (2018) vol. 48, Suppl. 1, pp. S39-S52.
Osier et al., "Chronic Histopathological and Behavioral Outcomes of Experimental Traumatic Brain Injury in Adult Male Aniamls," Journal of Neurotrauma (2015) vol. 32, No. 23, doi: 10.1089/neu. 2014.3680, 85 pages.
Pabón et al., "Brain Region-Specific Histopathological Effects of Varying Trajectories of Controlled CorticalImpact Injury Model of Traumatic Brain Injury," CNS Neurosceience & Therapeutics (2016) vol. 22, pp. 200-211.
Park et al., "Repeated Oral Administration of Human Serum Albumin Protects from the Cerebral Ischemia in Rat Brain Following MCAO," Exp Neurobiol (2017) vol. 26, No. 3, pp. 151-157.
Patel et al., "Acetyl-L-Carnitine Ameliorates Mitochondrial Dysfunction Following Contusion Spinal Cord Injury," J Neurochem (2010) vol. 114, No. 1, pp. 291-301.
Paterno et al., "Memory deficit in an object location task after mild TBI is associated with impaired early object exploration and both are restored by branched chain amino acid dietary therapy," Journal of Neurotrauma (2017) doi: 10.1089/neu.2017.5170, 26 pages.
Paterno et al., "Pathophysiology and Treatment of Memory Dysfunction after Traumatic Brain Injury," Curr Neurol Neurosci Rep (2017) vol. 17, No. 7, doi: 10.1007/s11910-017-0762-x, 26 pages.
Perasso et al., "In vivo neuroprotection by a creatine-derived compound: Phosphocreatine-Mg-complex acetate," Brain Research (2009) vol. 1285, pp. 158-163.
Perasso et al., "Therapeutic Use of Creatine in Brain or Heart Ischemia: Available Data and Future Perspectives," Medical Research Reviews (2011) doi:10.1002/med.20255, 28 pages.
Perez-Garcia et al., "PTSD-Related Behavioral Traits in a Rat Model of Blast-Induced mTBI Are Reversed by the mGluR2/3 Receptor Antagonist BCI-838," eNeuro (2018) doi: 10.1523/ENEURO. 0357-17.2018, 50 pages.
Persky et al., "Pharmacokinetics of the Dietary Supplement Creatine," Clin Pharmacokinet (2003) vol. 42, No. 6, pp. 557-574.
Peterson et al., "A behavioral and histological comparison of fluid percussion injury and controlled cortical impact injury to the rat sensorimotor cortex," Behav Brain Res (2015) vol. 294, pp. 254-263.
Petttegrew et al., "Acetyl-L-carnitine physical-chemical, metabolic, and therapeutic properties: relevance for its mode of action in Alzheimer's disease and geriatric depresssion," Molecular Psychiatry (2000) vol. 5, pp. 616-632.
Picq et al., "DMA Metabolism: Targeting the Brain and Lipoxygenation," Mol Neurobiol (2010) vol. 42, pp. 48-51.
Prass et al., "Improved reperfusion and neuroprotection by creatine in a mouse model of stroke," Journal of Cerebral Blood Flow & Metabolism (2007) vol. 27, pp. 452-459.
Prins et al., "The pathophysiology of traumatic brain injury at a glance," Disease Models & Mechanisms (2013) vol. 6, pp. 1307-1315.

(56) References Cited

OTHER PUBLICATIONS

Qu et al., "Treatment of Traumatic Brain Injury in Mice with Bone Marrow Stromal Cell-Impregnated Collagen Scaffolds," J Neurosurg (2009) vol. 111, No. 4, pp. 658-665.
Rangel-Castilla et al., "L-Arginine Reactivity in Cerebral Vessels After Severe Traumatic Brain Injury," Neurol Res (2010) vol. 32, No. 10, pp. 1033-1040.
Reis et al., "Phase I and Phase II Therapies for Acute Ischemic Stroke: An Update on Currently Studied Drugs in Clinical Research," BioMed Research International (2017) vol. 2017, Article 4863079, 14 pages.
Remington et al., "A Phase II Randomized Clinical Trial of a Nutritional Formulation for Cognition and Mood in Alzheimer's Disease," J Alzheimers Dis (2015) vol. 45, No. 2, pp. 395-405. Abstract Only.
Ruggeri et al., "The role of von Willebrand faction in thrombus formation," Thromb Res (2007) vol. 120, Supp. 1, pp. S5-S9.
Russo et al., "Distinct myeloid cell subsets promote meningeal remodeling and vascular repair after mild traumatic brain injury," Nat Immunol (2018) doi: 10.1038/s41590-018-0086-2, 13 pages.
Sakellaris et al., "Prevention of Complications Related to Traumatic Brain Injury in Children and Adolescents With Creatine Administration: An Open Label Randomized Pilot Study," J Trauma (2006) vol. 61, No. 2, pp. 322-329.
Sakellaris et al., "Prevention of traumatic headache, dizziness and fatigue with creatine administration. A pilot study," Acta Paediatrica (2008) vol. 97, pp. 31-34.
Salvador et al., "Stretch and/or oxygen glucose deprivation (OGD) in an in vitro traumatic brain injury (TBI) model induces calcium alteration and inflammatory cascade," Frontiers in Cellular Neuroscience (2015) vol. 9, Article 323, 14 pages.
Scafidi et al., "Neuroprotection by Acetyl-L-Carnitine after Traumatic Brain Injury to the Immature Rat Brain," Dev Neurosci (2010) vol. 32, pp. 480-487.
Schaar et al., "Functional assessments in the rodent stroke model," Experimental & Translational Stroke Medicine (2010) vol. 2, Article 13, 11 pages.
Scherbakov et al., "Influence of essential amino acids on muscle mass and muscle strength in patients with cerebral stroke during early rehabilitation: protocol and rationale of a randomized clinical trial (AMINO-Stroke Study)," BMC Neurology (2016) vol. 16, No. 10, 7 pages.
Schlattner et al., "Mitochondrial creatine kinase in human health and disease," Biochimica et Biophysica Acta (2006) vol. 1762, pp. 164-180.
Schooneman et al., "Acylcamitines: Reflecting or Inflicting Insulin Resistance?" Diabetes (2013) vol. 62, DOI: 10.2337/db12-0466, 8 pages.
Si et al., "Improved cognitive outcome after progesterone administration is associated with protecting hippocampal neurons from secondary damage studied in vitro and in vivo," Behavioural Brain Research (2014) vol. 264, pp. 135-142.
Si et al., "Progesterone treatment improves cognitive outcome following experimental traumatic brain injury in rats," Neuroscience Letters (2013) vol. 553, pp. 18-23.
Singh et al., "Oxygen Glucose Deprivation Model of Cerebral Stroke in PC-12 Cells: Glucose as a Limiting Factor," Toxicology Mechanisms and Methods (2008) doi: 10.1080/15376510802355l216, 7 pages.
Small et al., "Biology of Ischemic Cerebral Cell Death," Progress in Cardiovascular Diseases (1999) vol. 42, No. 3, pp. 185-207.
Smith et al., "Brain Injury Impairs Working Memory and Prefrontal Circuit Function," Frontiers in Neurology (2015) vol. 6, Article 240, 13 pages.
Sta Maria et al., "D-Cycloserine Restores Experience-Dependent Neuroplasticity after Traumatic Brain Injury in the Developing Rat Brain," Journal of Neurotrauma (2017) vol. 34, pp. 1692-1702.
Stein, "Embracing failure: What the Phase III progesterone studies can teach about TBI clinical trials," Brain Inj (2015) vol. 29, No. 11, pp. 1259-1272.
Stelmaschuk et al., "Amantadine to Treat Cognitive Dysfunction in Moderate to Severe Traumatic Brain Injury," Journal of Trauma Nursing (2015) vol. 22, No. 4, pp. 194-203.
Stern et al., "Preliminary Study of Plasma Exosomal Tau as a Potential Biomarker for Chronic Traumatic Encephalopathy," Journal of Alzheimer's Disease (2016) vol. 51, pp. 1099-1109.
Stevens et al., "Creatine protects against mitochondrial dysfunction associated with HIV-1 Tat-induced neuronal injury," Curr HIV Res (2015) vol. 12, No. 6, pp. 378-387.
Stout et al., "Effects of Creatine Supplementation on the Onset of Neuromuscular Fatigue Threshold and Muscle Strength in Eldery Men and Women (64-84 Years)," the Journal of Nutrition, Health & Aging (2007) vol. 11, No. 6, pp. 159-464.
Sullivan et al., "Dietary Supplement Creatine Protects against Traumatic Brain Injury," Ann Neurol (2000) vol. 48, pp. 723-729.
Tagge et al., "Concussion, microvascular injury, and early taupathy in young athletes after impact head injury and an impact concussion mouse model," Brain (2018) doi: 10.1093/brain/awx350, 37 pages.
Terpolilli et al., "The Novel Nitric Oxide Synthase Inhibitor 4 amino-tetrahydro L biopterine Prevents Brain Edema Formation and Intracranial Hypertension following Traumatic Brain Injury," Journal of Neurotrauma (2009) vol. 26, pp. 1963-1975.
Tymianski, "Novel Approaches to Neuroprotection Trials in Acute Ischemic Stroke," Stroke (2013) vol. 44, pp. 2942-2950.
Vergun et al., "Glutamate-induced mitochondrial depolarisation and perturbation of calcium homeostasis in cultured rat hippocampal neurones," Journal of Physiology (1999) vol. 519, No. 2, pp. 451-466.
Vink et al., "Magnesium attenuates persistent functional deficits following diffuse traumatic brain injury in rats," Neuroscience Letters (2003) vol. 336, pp. 41-44.
Vuille-Dit-Bille et al., "Changes in plasma phenylalanine, isoleucine, leucine, and valine are associated with significant changes in intracranial pressure and jugular venous oxygen saturation in patients with severe traumatic brain injury," Amino Acids (2012) vol. 43, pp. 1287-1296.
Wei et al., "NNZ-2566 treatment inhibits neuroinflammation and pro-inflammatory cytokine expression induced by experimental penetrating ballistic-like injury in rats," Journal of Neuroinflammation (2009) vol. 6, No. 19, 10 pages.
Welle et al., "Investigation the Early Detection of Traumatic Brain Injury," slide presentation at the Food and Drug Administration 2015 Science Writers Symposium, 11 pages.
Wong et al., "Biochemistry of Cerebral Ischemia," slide presentation, Nov. 24, 2015, 19 pages.
Woo et al., "Inhibition of MMP-3 or-9 suppresses lipopolysaccharide-induced expression of proinflammatory cytokines and iNOS in microglia," Journal of Neurochemistry (2008) vol. 106, pp. 770-780.
Wright et al., "Very Early Administration of Progesterone for Acute Traumatic Brain Injury," N Engl J Med (2014) vol. 371, No. 26, pp. 2457-2466.
Xiong et al., "Animal models of traumatic brain injury," Nat Rev Neurosci (2013) vol. 14, pp. 128-142.
Yan et al., "APX3330 Promotes Neurorestorative Effects after Stroke in Type One Diabetic Rats," Aging and Disease (2018) vol. 9, No. 5, 14 pages.
Yu et al., "Severity of controlled cortical impact traumatic brain injury in rats and mice dictates degree of behavioral deficits," Brain Res (2009) vol. 1287, pp. 157-163.
Zafonte et al., "Effect of Citicoline on Functional and Cognitive Status Among Patients With Traumatic Brain Injury," JAMA (2012) vol. 308, No. 19, pp. 1993-2000.
Zanelli et al., "Mechanisms of Ischemic Neuroprotection by Acetyl-L-camitine," Ann NY Acad Sci (2005) vol. 1053, pp. 153-161.
Zhang et al., "Fucoxanthin provides neuroprotection in models of traumatic brain injury via the Nrf2-ARE and Nrf2-authphagy pathways," Nat Sci Rep (2017) vol. 7, article 46763, 15 pages.
Zhang et al., "Neuroprotective Effects of Pre-Treatment with L-Carnitine and Acetyl-L-Carnitine on Ischemic Injury In Vivo and In Vitro," Int J Mol Sci (2012) vol. 13, pp. 2078-2090.

(56) References Cited

OTHER PUBLICATIONS

Zhou et al., "Erythropoietin regulates immune/inflammatory reaction and improves neurological function outcomes in traumatic brain injury," Brain and Beahvior (2017) vol. 7, Article e00827, 10 pages.
Zhu et al., "Prophylactic Creatine Administration Mediates Neuroprotection in Cerebral Ischemia in Mice," The Journal of Neuroscience (2004) vol. 24, No. 26, pp. 5909-5912.
Zivin, "Clinical Trials of Neuroprotective Therapies," Stroke (2007) vol. 38, Part 2, pp. 791-793.
Abbott Laboratories "Jevity Plus" (2016) pp. 1-2.

\* cited by examiner

AMINO ACID COMPOSITIONS AND THEIR USE FOR THE TREATMENT OF TRAUMATIC BRAIN INJURY

RELATED APPLICATIONS

This application is a U.S. National Phase Application under 35 U.S.C. § 371 of International Application No. PCT/US2018/029908, filed Apr. 27, 2018, which claims priority to U.S. Ser. No. 62/491,796 filed Apr. 28, 2017. The contents of the aforementioned applications are hereby incorporated by reference in their entirety.

BACKGROUND

Traumatic Brain Injury (TBI) is characterized by a disruption in the normal function of the brain due to an acute external force to the brain. TBI can be mild and not cause long term disability, but is also a major cause of death and disability worldwide. Branched chain amino acid (BCAA) supplementation has been shown to reverse the effects of TBI in mice, and there are many promising treatments being developed. However, there is still a need for therapeutics that can treat patients suffering from traumatic brain injury.

SUMMARY

Provided herein are compositions with defined amino acid components, useful for treating traumatic brain injury.

Also provided is a method of treating traumatic brain injury, comprising administering to a subject in need thereof an effective amount of a pharmaceutical composition comprising defined amino acid components, and a pharmaceutically acceptable carrier, described herein.

DETAILED DESCRIPTION

Terms used in the claims and specification are defined as set forth below unless otherwise specified.

It must be noted that, as used in the specification and the appended claims, the singular forms "a," "an" and "the" include plural referents unless the context clearly dictates otherwise.

DEFINITIONS

An "amino acid" refers to an organic compound having an amino group (—$NH_2$), a carboxylic acid group (—C(=O)OH), and a side chain bonded through a central carbon atom, and includes essential and non-essential amino acids, as well as natural and unnatural amino acids.

The proteogenic amino acids, shown below, are known by three- and one-letter abbreviations in addition to their full names. For a given amino acid, these abbreviations are used interchangeably herein. For example, Leu, L or leucine all refer to the amino acid leucine; Ile, I or isoleucine all refer to the amino acid isoleucine; Val, V or valine all refer to the amino acid valine; Arg, R or arginine all refer to the amino acid arginine; and Gln, Q or glutamine all refer to the amino acid glutamine. Likewise, the non-natural amino acid derivative N-acetylcysteine may be referred to interchangeably by "NAC" or "N-acetylcysteine." Amino acids may be present as D- or L-isomers. Unless otherwise indicated, amino acids referred to herein are L-isomers of amino acids.

TABLE 1

Amino acid names and abbreviations

| Amino acid | Three-letter | One-letter |
|---|---|---|
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A "pharmaceutical composition" described herein comprises at least one amino acid and a pharmaceutically acceptable carrier or excipient. In some embodiments, the pharmaceutical composition is used as a therapeutic, a nutraceutical, a medical food, or as a supplement.

The term "pharmaceutically acceptable" as used herein, refers to amino acids, materials, excipients, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A composition, formulation or product is "therapeutic" if it provides a beneficial clinical effect. A beneficial clinical effect can be shown by lessening the progression of a disease and/or alleviating one or more symptoms of the disease.

The term "effective amount" as used herein means an amount of an amino acid, or pharmaceutical composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of treatment, the nature of concurrent therapy, the particular active ingredient(s) being employed, the particular pharmaceutically-acceptable excipient(s) and/or carrier(s) utilized, and like factors with the knowledge and expertise of the attending physician.

A "unit dose" or "unit dosage" as used herein means an amount or dose of medicine prepared in an individual packet or container for convenience, safety, or monitoring. A "unit dose" or "unit dosage" comprises the drug product or drug products in the form in which they are marketed for use, with a specific mixture of active ingredients and inactive components (excipients), in a particular configuration (such as a capsule shell, for example), and apportioned into a particular dose.

A pharmaceutical composition can contain an amino acid in an amount of at least about 0.5 g, 1 g, 1.5 g, 2 g, 2.5 g, 3 g, 3.5 g, 4 g, 4.5 g, 5 g, 5.5 g, 6 g, 7 g, 8 g, 9 g, 10 g, 11 g, 12 g, 13 g, 14 g, 15 g, 20 g, 25 g, 30 g, 35 g, 40 g, 45 g, 50 g, 55 g, 60 g, 65 g, 70 g, 75 g, or more than 75 g.

Determination of Amino Acid Weight Percent and Amino Acid Ratios in a Composition The weight ratio of a particular amino acid or particular amino acids in a composition or mixture of amino acids is the ratio of the weight of the particular amino acid or amino acids in the composition or mixture compared to the total weight of amino acids present in the composition or mixture. This value is calculated by dividing the weight of the particular amino acid or of the particular amino acids in the composition or mixture by the weight of all amino acids present in the composition or mixture.

Pharmaceutical Compositions

One aspect of the present disclosure provides a pharmaceutical composition comprising defined amino acid components. These pharmaceutical compositions are made up of individual, or free, amino acids and amino acid derivatives, and may include one or more pharmaceutically acceptable excipients.

An aspect of the present disclosure provides a composition comprising free amino acids and one or more pharmaceutically acceptable excipients, wherein the amino acids consist of leucine, isoleucine and valine, plus one or more of:
  (i) arginine and lysine;
  (ii) glutamine, N-acetylcysteine and glycine;
  (iii) methionine; and
  (iv) proline,
as its defined amino acid components.

In some embodiments, the amino acids consist of leucine, isoleucine, valine, arginine, lysine, glutamine, N-acetylcysteine, glycine, methionine, and proline.

In some embodiments, the amino acids consist of leucine, isoleucine, valine, arginine, and lysine.

In some embodiments, the amino acids consist of leucine, isoleucine, valine, glutamine, N-acetylcysteine, and glycine.

In some embodiments, the amino acids consist of leucine, isoleucine, valine, arginine, lysine, glutamine, N-acetylcysteine, and glycine.

In some embodiments, the amino acids consist of leucine, isoleucine, valine, arginine, lysine, glutamine, N-acetylcysteine, glycine and methionine or proline.

In some embodiments, the amino acids consist of leucine, isoleucine, valine, arginine, lysine, glutamine, N-acetylcysteine, glycine, methionine and proline.

In some embodiments, the amino acids consist of leucine, isoleucine, valine, arginine, lysine, glutamine, N-acetylcysteine, and glycine.

In some embodiments, the total weight of amino acids present is between 5 g and 75 g.

Production of the Amino Acid Compositions

Amino acids used to make the compositions may be agglomerated, and/or instantized to aid in dispersal and/or solubilization.

The amino acid compositions of the present disclosure may be made using amino acids and amino acid derivatives from the following sources, or other sources may used: e.g., FUSI-BCAA™ Instantized Blend (L-Leucine, L-Isoleucine and L-Valine in 2:1:1 weight ratio), FUSIL™ Instantized L-Leucine, L-Arginine HCl, L-Glutamine and other amino acids may be obtained from Ajinomoto Co., Inc; N-acetylcysteine may be obtained from Spectrum Chemical.

To produce the amino acid compositions of the instant disclosure, the following general steps may be used: the starting materials (individual amino acids and excipients) may be blended in a blending unit, followed by verification of blend uniformity and amino acid content, and filling of the blended powder into stick packs or other unit dosage form. The content of stick packs or other unit dosage forms may be dispersed in water at time of use for oral administration.

Formulations

The pharmaceutical compositions of the present disclosure may be in a form suitable for oral use (for example as tablets, lozenges, hard or soft capsules, aqueous or oily suspensions, emulsions, dispersible powders or granules, syrups or elixirs, medical food products, nutraceuticals), for topical use (for example as creams, ointments, gels, or aqueous or oily solutions or suspensions), for administration by inhalation (for example as finely divided powder) or for parental administration (for example as a sterile aqueous or oily solution for intravenous, subcutaneous, intramuscular dosing or as a suppository for rectal dosing).

Excipients

The amino acid compositions of the present disclosure may be compounded or formulated with one or more excipients. Non-limiting examples of suitable excipients include a tastant, a flavorant, a buffering agent, a preservative, a stabilizer, a binder, a compaction agent, a lubricant, a dispersion enhancer, a disintegration agent, a flavoring agent, a sweetener, and a coloring agent.

In some embodiments, the excipient comprises a buffering agent. Non-limiting examples of suitable buffering agents include citric acid, sodium citrate, magnesium carbonate, magnesium bicarbonate, calcium carbonate, and calcium bicarbonate.

In some embodiments, the excipient comprises a preservative. Non-limiting examples of suitable preservatives include antioxidants, such as alpha-tocopherol and ascorbate, and antimicrobials, such as parabens, chlorobutanol, and phenol.

In some embodiments, the composition comprises a binder as an excipient. Non-limiting examples of suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, and combinations thereof.

In some embodiments, the composition comprises a lubricant as an excipient. Non-limiting examples of suitable lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

In some embodiments, the composition comprises a dispersion enhancer as an excipient. Non-limiting examples of suitable dispersants include starch, alginic acid, polyvinylpyrrolidones, guar gum, kaolin, xanthan gum, bentonite, purified wood cellulose, sodium starch glycolate, isoamorphous silicate, and microcrystalline cellulose as high HLB emulsifier surfactants.

In some embodiments, the composition comprises a disintegrant as an excipient. In some embodiments, the disintegrant is a non-effervescent disintegrant. Non-limiting examples of suitable non-effervescent disintegrants include starches such as corn starch, potato starch, pregelatinized and modified starches thereof, sweeteners, clays, such as bentonite, microcrystalline cellulose, alginates, sodium starch glycolate, gums such as agar, guar, locust bean, karaya, pecitin, and tragacanth. In some embodiments, the disintegrant is an effervescent disintegrant. Non-limiting examples of suitable effervescent disintegrants include sodium bicarbonate in combination with citric acid, and sodium bicarbonate in combination with tartaric acid.

In some embodiments, the excipient comprises a flavoring agent. Flavoring agents can be chosen from synthetic flavor oils and flavoring aromatics; natural oils; extracts from plants, leaves, flowers, and fruits; and combinations thereof. In some embodiments, the flavoring agent is selected from cinnamon oils; oil of wintergreen; peppermint oils; clover oil; hay oil; anise oil; eucalyptus; vanilla; citrus oil such as lemon oil, orange oil, grape and grapefruit oil; and fruit essences including apple, peach, pear, strawberry, raspberry, cherry, plum, pineapple, and apricot.

In some embodiments, the excipient comprises a sweetener. Non-limiting examples of suitable sweeteners include glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; Stevia Rebaudiana (Stevioside); chloro derivatives of sucrose such as sucralose; and sugar alcohols such as sorbitol, mannitol, sylitol, and the like. Also contemplated are hydrogenated starch hydrolysates and the synthetic sweetener 3,6-dihydro-6-methyl-1,2,3-oxathiazin-4-one-2, 2-dioxide, particularly the potassium salt (acesulfame-K), and sodium and calcium salts thereof.

In some embodiments, the composition comprises a coloring agent. Non-limiting examples of suitable color agents include food, drug and cosmetic colors (FD&C), drug and cosmetic colors (D&C), and external drug and cosmetic colors (Ext. D&C). The coloring agents can be used as dyes or their corresponding lakes.

Particular excipients may include one or more of: citric acid, lecithin, (e.g. Alcolec F100), sweeteners (e.g. sucralose, sucralose micronized NF, acesulfame potassium (e.g. Ace-K)), a dispersion enhancer (e.g. xanthan gum (e.g. Ticaxan Rapid-3)), flavorings (e.g. vanilla custard #4306, Nat Orange WONF #1326, lime 865.0032U, and lemon 862.2169U), a bitterness masking agent (e.g. 936.2160U), and natural or artificial colorings (e.g. FD&C Yellow 6).

Methods of Treatment

One aspect of the present disclosure provides methods of treating traumatic brain injury, comprising administering to a subject in need thereof an effective amount of a pharmaceutical composition described herein.

The compositions of the present disclosure may be tested via a variety of known traumatic brain injury animal models such as fluid percussion injury (Cole et al, 2010; 366-371, PNAS, Jan. 5, 2010, vol. 107, no. 1) and controlled cortical impact (Romine et al, 2014; J. Vis. Exp. 2014 Aug. 5;(90): e51781) models. The compositions may also be tested in the clinic according to the protocol clinicaltrials.gov ID: NCT01860404 by Akiva Cohen from University of Pennsylvania, which tests reaction times after administration of treatment within 72 hours of the injury.

An aspect of the present disclosure provides a method for treating traumatic brain injury comprising administering to a subject in need thereof an effective amount of a composition described herein.

An aspect of the present disclosure provides a composition described herein for use as a medicament.

An aspect of the present disclosure provides a composition described herein for use as a medicament in the treatment of traumatic brain injury.

An aspect of the present disclosure provides a use of a composition described herein for the manufacture of a medicament for treatment of traumatic brain injury.

In some embodiments, the subject has been diagnosed with traumatic brain injury.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

The invention claimed is:

1. A composition comprising free amino acids and one or more pharmaceutically acceptable excipients, wherein the amino acids consist of leucine, isoleucine and valine, plus one or more of:
   a. both of arginine and lysine;
   b. all of glutamine, N-acetylcysteine and glycine;
   c. methionine; and
   d. proline,
as its defined amino acid components.

2. The composition of claim 1, wherein the amino acids consist of leucine, isoleucine, valine, arginine, lysine, glutamine, N-acetylcysteine, glycine, methionine, and proline.

3. The composition of claim 1, wherein the amino acids consist of leucine, isoleucine, valine, arginine, and lysine.

4. The composition of claim 1, wherein the amino acids consist of leucine, isoleucine, valine, glutamine, N-acetylcysteine, and glycine.

5. The composition of claim 1, wherein the amino acids consist of leucine, isoleucine, valine, arginine, lysine, glutamine, N-acetylcysteine, and glycine.

6. The composition of claim 1, wherein the amino acids consist of leucine, isoleucine, valine, arginine, lysine, glutamine, N-acetylcysteine, glycine, and methionine or proline.

7. The composition of claim 1, wherein the total weight of amino acids present is between 5 g and 75 g.

8. The composition of claim 1, wherein the composition is a pharmaceutical composition comprising one or more pharmaceutically acceptable excipients.

* * * * *